United States Patent [19]

Amiji

[11] Patent Number: 5,885,609
[45] Date of Patent: Mar. 23, 1999

[54] BIOCOMPATIBLE ARTICLES AND METHOD FOR MAKING SAME

[75] Inventor: Mansoor M. Amiji, Attleboro, Mass.

[73] Assignee: Northeastern University, Boston, Mass.

[21] Appl. No.: 862,854

[22] Filed: May 23, 1997

[51] Int. Cl.[6] .............................. A61F 13/02; A61L 15/16; A61K 9/50

[52] U.S. Cl. .......................... 424/425; 424/435; 424/447; 424/499; 424/501; 424/502

[58] Field of Search ..................................... 424/423, 424, 424/435, 447, 499, 501, 502, 425

[56] References Cited

U.S. PATENT DOCUMENTS

| | | | |
|---|---|---|---|
| 5,208,166 | 5/1993 | Saunders et al. | 436/518 |
| 5,620,706 | 4/1997 | Dumitriu et al. | 424/485 |

FOREIGN PATENT DOCUMENTS 96 20698  11/1996  WIPO .............................. A61K 9/51

OTHER PUBLICATIONS

Beena et al, "Phenyl Alanine, Tryptophan Immobilized Chitosan Beads as Adsorbents for Selective Removal of Immunoproteins", J. of Biomaterials Applications, 8:385–402, 1994.

Chandy et al., "Polylysine–Immobilized Chitosan Beads as Adsorbents for Bilirubin", Artificial Organs, 6:568–576, 1992.

Amiji, "Surface Modification of Chitosan Membranes by Complexation–Interpenetration of Anionic Polysaccharides for Improved Blood Compatibility in Hemodialysis", J. Biomater. Sci Polymer Edn., 8:281–298, 1996.

Amiji, "Modification of Chitosan Membrane Surfaces by Complexation–Interpenetration of Anionic Polysaccharides", Surfaces in Biomaterials Conference, pp. 108–112, 1996.

Amiji, "Surface Modification of Chitosan Hemodialysis Membranes with Anionic Polysaccharides", Fifth World Biomaterials Congress, 1:879, 1996.

Desai et al., "Surface Physical Interpenetrating Networks of Poly(ethylene terephthalate) and Poly(ethylene oxide) with Biomedical Applications", Macromolecules, 25:226–232, 1992.

Piehler et al., "Surface Modification for Direct Immunoprobes", Biosensors & Bioelectronics, 11:579–590, 1996.

*Primary Examiner*—Carlos A. Azpuru
*Attorney, Agent, or Firm*—Weingarten, Schurgin, Gagnebin & Hayes LLP

[57] ABSTRACT

Articles of manufacture and methods of making the same, comprising a cationic polymer which has been surface-modified by a method comprising the steps of swelling a cationic polymer in a medium having a pH value <7; applying a surface-modifying agent to the cationic polymer to form a mixture; and adjusting the pH of the mixture to a value $\geq 7$. A preferred embodiment relates to semipermeable membranes suitable for hemodialysis made from chitosan, the surface of which has been modified by anionic polysaccharides such as dextran or heparin, or anionic polyoxyalkylenes such as acid-modified polyethylene glycol, to improve blood compatibility.

18 Claims, 2 Drawing Sheets

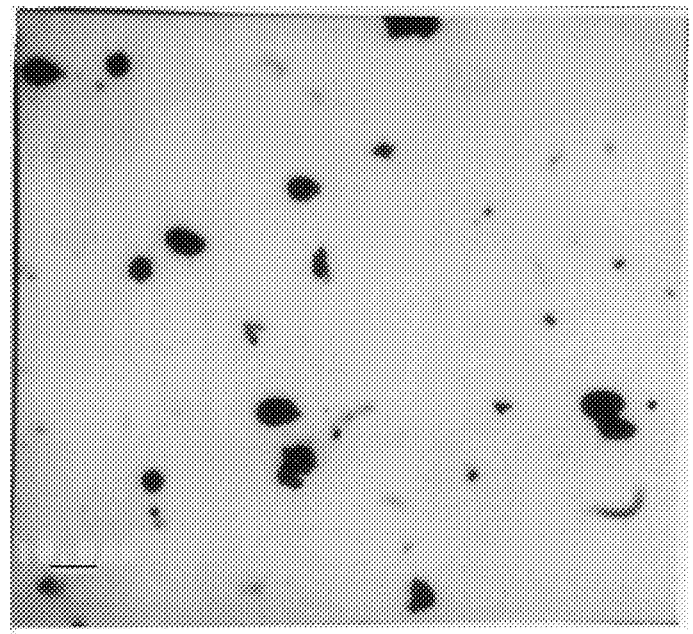
FIG. IC
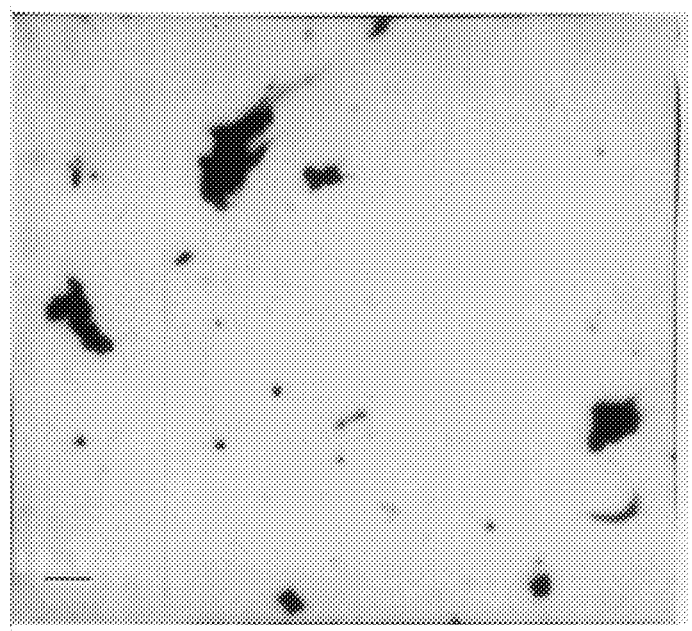
FIG. ID

BIOCOMPATIBLE ARTICLES AND METHOD FOR MAKING SAME

BACKGROUND OF THE INVENTION

Hemodialysis is an important clinical procedure for the removal of toxic biological metabolites in patients with end-stage renal disease. The central element of a hemodialysis instrument is the semipermeable membrane which allows for selective transport of low molecular weight biological metabolites, in particular urea and creatinine, from blood. The semipermeable membranes used in hemodialysis instruments may be made from natural or synthetic polymeric materials. Cellulose is used almost exclusively to make the natural hemodialysis membranes. Synthetic membranes are typically made from hydrophobic [e.g., (poly (methyl methacrylate) and polycarbonate] and hydrophilic (e.g., polyacrylonitrile and polysulfone) polymers. Currently, most clinically used hemodialysis instruments are equipped with cellulosic membranes.

Surface-induced thrombosis and serum complement activation are two of the most serious consequences of blood-cellulose membrane interactions in hemodialysis. Thrombosis is initiated by the adsorption of plasma proteins, followed by the adhesion and activation of platelets. When activated, platelets secrete adenosine diphosphate (ADP), serotonin, and other granular contents to activate other resting platelets and the coagulation cascade reaction. Platelet activation results in mural thrombus formation on hemodialysis membranes, potentially embolizing into the blood stream. Currently, surface-induced thrombosis is minimized by heparin infusion during the hemodialysis procedure. Large doses of heparin needed for anticoagulation can lead to uncontrolled bleeding episodes that can be fatal.

The complement system acts as a first line defense mechanism against microbial infections and the presence of foreign materials in the body. The complement system, consisting of 30 different proteins, can be activated by the classical pathway or the alternative pathway. Cellulose-based membranes are known to activate the alternative pathway of the complement system due to covalent interaction between the C3b fragment of complement and the surface-accessible hydroxyl groups of cellulose. Complement activation leads to a transient decrease in white blood cell count observed during 30 m of treatment. Release of cytokines and other biological mediators by complement activation may also lead to downstream complications such as hemodialysis intolerance, pulmonary hypertension, and immune suppression.

Since the interactions leading to thrombosis and complement activation occur at the blood-membrane interface, attempts have been made to modify cellulose membrane surfaces by covalent grafting of poly(ethylene glycol), $C_{16}$–$C_{18}$ alkyl chains to selectively adsorb albumin from plasma, and heparin to improve blood compatibility. Surface modification of cellulose membranes by covalent grafting assures that the modifying agent will not be removed or displaced during blood contact. Unfortunately, the methods of covalent grafting are cumbersome and, in some cases, require the use of toxic organic solvents. Furthermore, the covalently-modified cellulose membranes could have lower permeability profiles than the unmodified membranes.

Cationic polymers such as chitosan have been proposed for the development of membranes and fibers for hemodialysis and blood oxygenators, skin substitute and wound dressing material, as a matrix for immobilization of enzymes and cells, for binding with bile and fatty acids, and as a vehicle for drug and gene delivery. Chitosan, a linear polymer of D-glucosamine, is obtained by alkaline N-deacetylation of chitin. Chitosan has excellent film forming properties and high mechanical strength which make it suitable for hemodialysis membranes. Unfortunately, however, chitosan promotes plasma protein adsorption, platelet adhesion and activation, and thrombus development.

Therefore, it would be desirable to employ cationic polymers such as chitosan in making biocompatible articles such as membranes and fibers for hemodialysis and blood oxygenators, skin substitute and wound dressing material, etc., which have the advantages of the base material, but avoid the use of covalent surface modification techniques, but offer long-term blood compatibility of covalently-modified membranes.

BRIEF SUMMARY OF THE INVENTION

This invention relates in general to articles made of cationic polymers such as chitosan, and in particular to methods of surface treatment to make biocompatible articles such as hemodialysis membranes.

The disclosure relates to articles of manufacture and methods of making the same, comprising a cationic polymer which has been surface-modified by a method comprising the steps of swelling a cationic polymer article in a medium having a pH value <7; applying a surface-modifying agent to the cationic polymer to form a mixture; and adjusting the pH of the mixture to a value $\geq 7$. In one advantageous embodiment, semipermeable membranes suitable for hemodialysis are made from chitosan, the surface of which has been modified by complexation-interpenetration of, e.g., anionic polysaccharides such as dextran or heparin, or anionic polyoxyalkylenes such as acid-modified polyethylene glycol, to improve blood compatibility.

BRIEF DESCRIPTION OF THE DRAWINGS

The invention will be more fully understood by reference to the following Detailed Description Of The Invention in conjunction with the following Drawing(s), of which:

FIGS. 1(a)–1(d) are comparative micrographs showing platelet adhesion and activation to cellulose; untreated chitosan; and two surface modified chitosan surfaces made in accordance with the invention.

DETAILED DESCRIPTION OF THE INVENTION

Figure 1A:
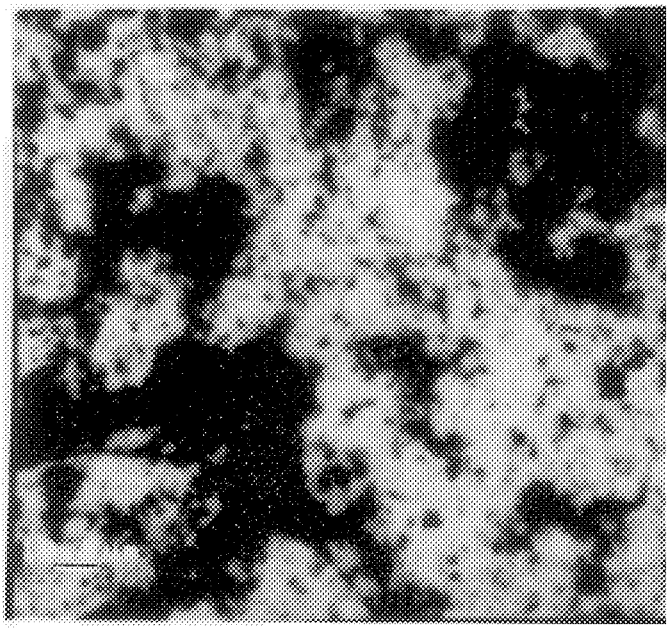

The useful articles disclosed herein comprise a cationic polymer having ionizable functional groups such as —$NH_2$, and which swell and ionize at low pH, e.g., <7. The cationic polymers may be natural or synthetic in origin. Cationic polymers which may be used include chitosan; cationic cellulose derivatives such as UCARE® (Union Carbide); and cationic polyacrylates such as Eudragit® (Rohm and Haas) and poly(dimethylaminoethyl methacrylate).

The surface modification method disclosed herein allows for non-covalent surface modification. The method involves swelling an article comprising a cationic polymer in acidic pH medium; adding the surface-modifying agent to form a mixture and allow the surface modifying agent to cover and penetrate the surface; then raising the pH of the system to neutrality or alkalinity, i.e., $\geq 7$ to "collapse" the article and consequently immobilize the surface-modifying agent on the surface of the article.

Suitable surface-modifying agents include anionic polysaccharides such as heparin and dextran sulfate; anionic polyalkylene oxide derivatives; anionic polyalkylene glycol derivatives such as methoxypoly(ethylene glycol) sulfonate (MPEG sulfonate); polycarboxylic acids; anionic surfactants; anionic phospholipids; carboxyalkylcelluloses; and mixtures thereof. Other specific examples of the above include alginic acid, hyaluronic acid, carboxymethylcellulose, acid-modified polyethylene glycol, and acid-modified polyethylene oxide.

Since the interactions that lead to surface-induced thrombosis occur at the blood-biomaterial interface, surface modification as disclosed herein prevents plasma protein adsorption, platelet adhesion, and thrombus formation; this property is theorized, to occur by the steric repulsion mechanism, although this theory is not meant to be limiting on the invention. Steric repulsion by surface-bound water-soluble polymer chains occurs as a result of overlapping polymer layers which could lead to loss in configurational entropy because of volume restriction and/or osmotic repulsion between interdigitated polymer chains. For effective steric repulsion, the surface-modifying agent desirably satisfies the following three requirements. First, the polymer chains (i.e., surface-modification agent) should be tightly bound to the surface. Second, some part of the surface-bound polymer must extend into the bulk medium, as the dominance of steric repulsion over van der Waals attractive forces occurs only when the polymer chains have extended into the bulk medium. Finally, the surface should be fully covered with the modifying agent. Steric repulsion tends to be ineffective if a significant portion of the surface is unmodified.

Surface modified cationic polymers in accordance with the invention are contemplated to have a number of non-limiting uses, as set forth below:

1. Liquid as a coating material for medical devices. Solutions of biocompatible surface-modified cationic polymers can be used as a coating material for medical and pharmaceutical devices to prevent protein adsorption and cell adhesion. Such coating solutions can also be used to prevent non-specific protein adsorption and cell adhesion on microtiter plates and other laboratory devices.
2. Membranes and hollow fibers for hemodialysis and blood oxygenators. Chitosan, like cellulose, has film-forming properties and high mechanical strength for membrane and fiber production. These articles can be made biocompatible by surface modification as disclosed without any alteration in permeability.
3. Films and sponges for artificial skin, wound dressing materials, and as physical barriers to prevent post-surgical adhesions. Such films have the potential for use as skin substitutes. The hemostatic activity of chitosan, for example, mediated probably by platelet adhesion and activation, favors its use as a wound dressing material. Films and sponges, when placed in hollow organs, prevent non-specific adhesion after surgery.
4. Biocompatible and biodegradable fibers and threads for suture material in wound closure.
5. Microcapsules for protein and cell immobilization. Microcapsules, formed by complex coacervation, can be used to package proteins and cells.
6. Microspheres and nanospheres for immuno-adsorption and drug delivery. Beads of surface-modified cationic polymer may be fabricated for use in immunoaffinity columns for, e.g., removing bilirubin and other toxic compounds from blood. They can also be used for drug, genes, and vaccine delivery in the body.
7. Rods (hollow or solid) as stents for the treatment of restinosis after coronary angioplasty and for drug, genes, and vaccine delivery in the body. The retraction of coronary artery after balloon angioplasty requires implantation of a stent. Biocompatible cationic polymer stents can be fabricated by the disclosed method either in the absence or presence of drugs for targeted delivery. In addition, drugs, genes, or vaccines can be loaded into the solid rods as an implantable delivery system.
8. Paste for bone regeneration. Studies have shown that chitosan-calcium phosphate paste can be used to facilitate bone regeneration and for drug delivery to the bone in cases of infections and cancer.

The following non-limiting examples are intended to describe and demonstrate the utility set forth herein of the invention and in the appended claims.

EXAMPLE 1

A. Membrane Preparation and Characterization

Preparation of Chitosan Membranes: Chitosan membrane with an average wet thickness of 50 μm was prepared as follows: Chitosan ($M_v$=1,000,000) with a degree of deacetylation of 87%, obtained from Pronova Biopolymers (Raymond, Wash.), was dissolved in 0.1M acetic acid to prepare a 1.0% (w/v) solution. The solution was filtered through glass wool and degassed overnight. Twenty ml of chitosan solution was poured into a disposable polystyrene petri dish and spread to produce a thin film. The solvent was evaporated at room temperature and the membrane was neutralized in 1.0M NaOH. After extensive washing with deionized distilled water to remove residual NaOH, the membranes were stored at 4° C. in phosphate-buffered saline (PBS, pH 7.4) containing 0.02% (w/v) sodium azide as a preservative.

Swelling and Thickness Measurements: The degree of swelling and change in thickness of chitosan membranes in acidic and neutral solutions was measured. Chitosan membranes were swollen in 10 mM acetic acid or PBS solution for 10 minutes. The percent water uptake was calculated according to the following expression:

$$\% \text{ Water Uptake} = [(W_s - W_d)/(W_s)] \times 100$$

where $W_s$ is the weight of the swollen membrane and $W_d$ is the weight of the air-dried membrane. The change in wet-thickness of the membrane in contact for 10 minutes in acetic acid or PBS solution was measured with a Mitutoyo (Tokyo, Japan) digital micrometer. The micrometer was calibrated to an accuracy of ±1.0 μm. The results of swelling and thickness represent average ± S.D. from at least four membrane samples.

Electron Spectroscopy for Chemical Analysis: The surface atomic composition of control and dextran sulfate-modified chitosan membranes were characterized by electron spectroscopy for chemical analysis (ESCA), to measure the elemental composition and identify the chemical functional groups on the membrane surface at 100 Å depth. Analysis was performed using an X-Probe ESCA instrument (Surface Science Instruments, Mountain View, Calif.) equipped with an aluminum $K_{\alpha 1,2}$ monochromatized X-ray source. An electron flood gun set at 5 eV was used to minimize surface charging. Surface elemental composition was determined using the standard Scofield photoemission cross-sections.

B. Surface Modification

Heparin sodium ($M_v$=15,000 daltons, 179 units/mg), isolated from porcine intestinal mucosa, was purchased from Sigma Chemical Company (St. Louis, Mo.). The sodium salt of dextran sulfate ($M_v$=500,000 daltons) was purchased from Polysciences, Inc. (Warrington, Pa.). Based on the preliminary results of platelet adhesion and activation (described below under Blood Compatibility Studies), the membranes were modified with 2.5 mg/ml and 10 mg/ml of the anionic polysaccharides heparin and dextran sulfate. The pH values of heparin and dextran sulfate solutions were 7.32 and 7.54, respectively, at 10 mg/ml concentration. For complexation/interpenetration, the chitosan membrane was allowed to swell in 10 mM acetic acid for 10 minutes. The membrane was removed from the swelling medium and transferred into a glass petri dish containing either heparin or dextran sulfate solution. The membrane was manually unfolded to allow complete surface coverage during the modification process. Following a brief period (~20 seconds) of complexation of the anionic polysaccharides with the cationic chitosan surface and interpenetration into the swollen chitosan matrix, 1.0 ml of 0.1M NaOH was added to raise the pH of the medium to collapse the swollen membrane and entrap the modifying agent on the membrane surface. The modified membranes were washed with deionized distilled water and stored in PBS at 4° C. The size and thickness of the membrane after modification did not change, suggesting no alteration in the membrane induced by the swelling in 10 mM acetic acid solution.

C. Permeability Studies

The permeability coefficient of five analytes (with increasing molecular weight) was determined through chitosan and surface-modified chitosan membranes at room temperature using a dialysis apparatus. Commercially available cellulose hemodialysis membrane (Cuprophan®, Akzo-Faser, Wüppertal, Germany) was used as a control. Urea (Mol. Wt. 60), creatinine (Mol. Wt. 113), glucose (Mol. Wt. 180), vitamin B-2 (riboflavin, Mol. Wt. 376), and vitamin B-12 (cyanocobalamine, Mol. Wt. 1355) solutions with a concentration of 1.0 mg/ml, 0.1 mg/ml, 1.5 mg/ml, 0.1 mg/ml, and 0.2 mg/ml, respectively, were prepared in PBS. Two hundred ml of the solution was placed in the donor compartment of the dialysis apparatus. The receptor compartment, separated by the membrane, was filled with 200 ml of PBS. Both sides of the dialysis apparatus were continuously stirred to assure uniform analyte distribution during the experiment. At pre-determined time intervals, 3 ml of the sample from the receptor compartment was removed and replaced with 3 ml of fresh PBS. Diacetyl monooxime and o-toluidine reagents were used to complex with urea and glucose, respectively, in order to determine the concentration of these analytes in the receptor compartment as a function of time. The absorbance of urea-diacetyl monooxime complex and glucose-o-toluidine complex was measured with a Shimadzu 160U UV/VIS spectrophotometer at 535 nm and 630 nm, respectively. Creatinine, vitamin B-2, and vitamin B-12 concentrations were measured directly from the absorbance at 235 nm, 445 nm, and 361 nm, respectively. The concentration of each compound in the receptor compartment was calculated from the appropriate calibration curves. The permeability coefficients of these compounds through Cuprophan, chitosan, and surface-modified chitosan membranes were calculated according to the following equation:

$$\ln (C_o/C_t) = PSt/lV$$

where $C_o$ is the initial concentration of the permeant in the donor compartment, $C_t$ is the concentration at any time t, P is the permeability coefficient (in cm²/min), S is the surface area of the membrane (12.57 cm²), V is the volume of solution in the donor compartment (200 ml), and l is the wet-thickness of the membrane (45 to 50 μm). Plots of ln $(C_o/C_t)$ versus (dialysis time/membrane thickness) were constructed and the slope of the line was used to calculate P. The results represent the average permeability coefficient ± S.D. of the analyte through control and surface-modified membranes from at least three independent experiments.

D. Blood Compatibility Studies

Serum Complement Activation: Human blood was obtained from healthy adult volunteers after informed consent. Blood was collected in evacuated containers (Vacutainers®, Becton-Dickinson, Rutherford, N.J.) in the absence of anticoagulant. After 1 h at 4° C., the clotted blood was centrifuged at 2000 g for 20 minutes to separate the serum. Hydrated Cuprophan, chitosan, or surface-modified chitosan membrane, with an approximate surface area of 80 cm², was incubated in 2.0 ml of serum at 37° C. for 1 h. The concentration of complement component iC3b in the serum was determined using a commercially available enzyme immunoassay (Quidel, San Diego, Calif.). One hundred μl of the diluted (1:50) serum from each sample was placed in a well of an anti-human iC3b monoclonal antibody-coated 96-well microplate. Following antigen interactions with immobilized iC3b antibody, horseradish peroxidase-conjugated anti-iC3b was added, followed by the addition of the chromogenic substrate. The absorbance at 405 nm was measured using a SPECTRAmax® microplate reader (Molecular Devices, Sunnyvale, Calif.). The data represent average ± S.D. from three independent experiments.

Platelet Adhesion and Activation: For platelet adhesion studies, chitosan membranes with an approximate thickness of 7–10 μm, were cast on a 25×75 mm glass microscope slide. Glass slides, cleaned with 2.0% (v/v) Isoclean® solution (Isolab, Akron, Ohio.), were dip-coated with 1.0% (w/v) chitosan solution in 0.1M acetic acid. Chitosan-coated slides were neutralized with sodium hydroxide and washed extensively with deionized distilled water as described above. In addition, heparin- and dextran sulfate-modified chitosan membranes were prepared as described above under "Surface Modification". An observation chamber for adherent platelets was assembled consisting of Cuprophan, chitosan, or surface-modified chitosan slide, two polyethylene spacers, and a glass cover slip.

Human blood obtained from healthy volunteers as described above, was collected in heparin-containing evacuated containers. Heparinized blood was centrifuged at 100 g for 10 minutes to obtain platelet-rich plasma (PRP). Two-hundred μl of PRP was instilled into the platelet observation chamber. Platelets in PRP were allowed to adhere and activate on Cuprophan, chitosan, and surface-modified chitosan slides for 1 h at room temperature. Non-adherent platelets and plasma proteins were removed by washing the chamber with PBS. Adherent platelets were fixed with 2.0% (w/v) glutaraldehyde solution in PBS for 1 h. After washing with PBS, the platelets were stained with 0.1% (w/v) Coomassie Brilliant Blue (Bio-Rad) dye solution for 1.5 h. Stained platelets were observed using a Nikon Labophot II (Melville, N.Y.) light microscope at 40× magnification. The image of adherent platelets was transferred to a Sony Trinitron video display using a Hamamatsu CCD camera. The Hamamatsu Argus-10 image processor was used to calculate the number of platelets per 25,000 μm² surface area in every field of observation. The results represent an average ± S.D. of the platelet count from twelve different fields of observation per experiment and at least two independent experiments. The extent of platelet activation was determined qualitatively from the spreading behavior of adherent platelets.

Plasma Recalcification Time: For recalcification time measurements, 16×100 mm clean glass test tubes were coated with chitosan and the surface was modified with heparin or dextran sulfate as described above. Blood was collected in sodium citrate-containing evacuated containers. Citrated blood was centrifuged at 2000 g for 20 minutes to obtain platelet-poor plasma. Plasma recalcification time of citrated plasma in contact with control and surface-modified chitosan was measured as follows. 1.0 ml of citrated plasma was mixed with 0.5 ml of 0.05M calcium chloride and incubated with Cuprophan, chitosan, and surface-modified chitosan in a water-bath at 37° C. The test tubes were occasionally removed from the water-bath and gently stirred. The time required for fibrin clot formation was recorded. The data indicates average of the plasma recalcification time ± S.D. from four independent experiments.

RESULTS

Membrane Characterization (Assessment of Swelling and Permeability Studies)

As shown in Table 1, there was an 87% increase in the solvent uptake by the membranes in 10 mM acetic acid for 10 minutes as compared to that in PBS. In addition, the thickness of the membrane in acidic solution was 33% greater than in neutral solution. The change in thickness of the membrane in acidic solution was relatively uniform, suggesting isotropic swelling of the membrane. It is theorized that as the positively charged chitosan membrane swells in acidic medium due to electrostatic repulsion between like charges and the osmotic effect of bound counterions, the anionic polysaccharide chains diffuse into the swollen matrix and interpenetrate with the chitosan chains. Following polyelectrolyte complexation and interpenetration, the addition of strong base to increase the pH of the medium and rapidly collapse the swollen membrane leads to entrapment of the modifying agent onto the surface, confirmed by ESCA. The surface density of the modifying agent was varied by selecting the bulk concentration of heparin and dextran sulfate of 2.5 mg/ml or 10 mg/ml.

Permeability Studies

The permeability coefficients of urea and creatinine, as shown in Table 2, were similar through chitosan membranes as in Cuprophan membranes. For low molecular weight uremic toxins like urea and creatinine, chitosan membrane has similar permeability profile as clinically-used Cuprophan membrane. When the solute molecular weight was increased, as with glucose, vitamin B-2, and vitamin B-12, the permeability coefficient in chitosan membranes was lower than that in Cuprophan membranes.

Surface modification of chitosan membrane with heparin at a bulk concentration of 2.5 mg/ml and 10 mg/ml did not appear to significantly alter the permeability coefficients of urea and creatinine. The presence of surface-bound heparin, however, did decrease the average permeability coefficient of glucose from $1.95 \times 10_{-5}$ cm$^2$/min in unmodified chitosan to $1.56 \times 10_{-5}$ cm$^2$/min in heparin-modified chitosan membranes at a bulk concentration of 2.5 mg/ml. The permeability coefficients of vitamin B-2 and vitamin B-12 also decreased after surface modification with heparin. In dextran sulfate-modified membranes, the permeability of vitamin B-2 decreased as well from that in unmodified chitosan membranes. The average permeability coefficient of vitamin B-12 was almost 95% lower in dextran sulfate-modified membranes at bulk concentration of 10 mg/ml as compared to the unmodified chitosan membrane.

The permeability coefficient of vitamin B-12 in chitosan membrane that was swollen in 10 mM acetic acid and collapsed with sodium hydroxide in the absence of surface modifying agents was the same as that in unmodified chitosan. The reduction in permeability coefficients observed in surface-modified membranes, therefore, appears to be due to the presence of anionic polysaccharides on the membrane surface. It is theorized that the presence of anionic polysaccharides form surface crosslinks with the cationic chitosan membrane to decrease the effective pore size for analyte diffusion. Furthermore, an additional diffusional layer created by the anionic polysaccharides on the membrane could also decrease the permeability of the compounds. In hemodialysis applications, it is therefore important to insure that the permeability of uremic toxins will not be altered significantly by surface modification of the membrane.

Blood Compatibility Studies

The extent of serum complement activation, platelet adhesion and activation, and plasma recalcification time were used to assess the in vitro blood compatibility of heparin and dextran sulfate-modified membranes. Cuprophan is known to activate the alternative pathway of the complement system due to the presence of surface hydroxyl groups. The serum iC3b concentration of 101.5 µg/ml in contact with Cuprophan membranes, as shown in Table 3, was consistent with the values obtained in the literature. The serum iC3b concentration in contact with unmodified chitosan membrane at 63.2 µg/ml was significantly lower than that with Cuprophan. Chitosan does not activate the complement system to the same extent as Cuprophan probably due to the presence of amine groups instead of hydroxyl groups on the surface. The iC3b concentration on heparin- and dextran sulfate-modified chitosan membranes in accordance with the invention was even lower than on the unmodified chitosan membrane. For heparin-modified membranes the iC3b concentration was 59.6 µg/ml and 51.4 µg/ml on membranes modified with 2.5 mg/ml and 10 mg/ml heparin, respectively. Compared to the iC3b concentration of serum in contact with unmodified chitosan, there was approximately 18% decrease in iC3b concentration in heparin-modified membranes. The serum iC3b concentration in contact with dextran sulfate-modified membrane was similar to the iC3b concentration on unmodified chitosan.

Platelet adhesion and activation is an indicator of the thrombogenicity of blood-contacting biomaterials. Table 4 shows the number of adherent platelets on Cuprophan, chitosan, and surface-modified chitosan membranes per 25,000 µm$^2$ surface area. Cuprophan membrane does promote thrombosis as more than 40 fully-activated platelets did adhere to this surface (Table 4). The number of adherent platelets was even higher on chitosan membranes. Nearly 60 fully-activated platelets were present probably due to the positive charges on the membrane surface. Surface modification of chitosan with anionic polysaccharides significantly reduced the number of adherent platelets and the extent of platelet activation. On heparin-modified surfaces, an average of 10 to 13 contact-adherent platelets were present per 25,000 µm$^2$ area. On the average, only 8 contact-adherent platelets were present on dextran sulfate-modified membranes (Table 4).

Figure 1B:
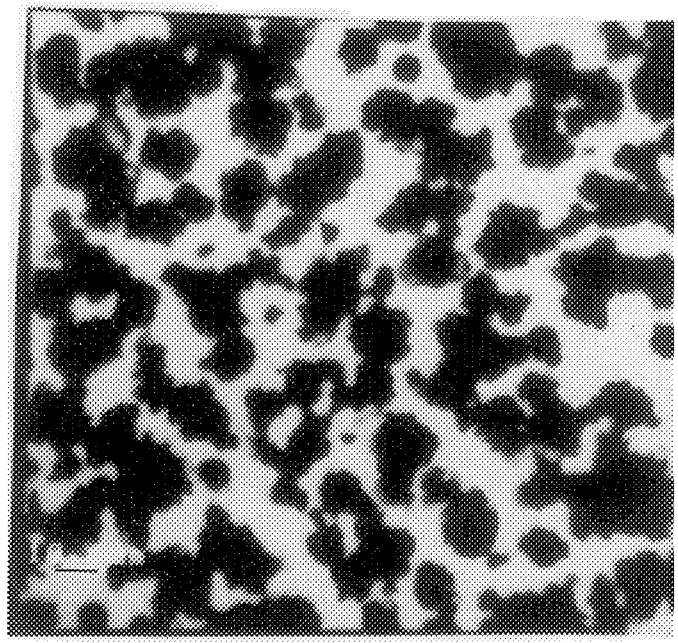

FIGS 1(a)–1(d) are micrographs which further illustrate the anti-thrombogenic nature of cationic polymers prepared in accordance with the invention, showing significant platelet adhesion and activation to cellulose (FIG. 1(a)) and untreated chitosan (FIG. 1(b)), and reduced platelet adhesion and activation to chitosan surface-modified with 2.5 g/ml dextran sulfate (FIG. 1(c)) and 10 g/ml dextran sulfate (FIG. 1(d)).

Plasma recalcification time is a measure of the intrinsic coagulation mechanism. Since the time required for contact activation of plasma varies with the type of surface, the plasma recalcification time is used as an indicator of blood compatibility of biomaterials. Plasma recalcification time of Cuprophan, as shown in Table 5, was approximately 10 minutes. Chitosan membranes also allowed the clot to form after about 9 minutes. Surface modification of chitosan with anionic polysaccharides, however, did significantly shorten the plasma recalcification time. In contact with heparin-modified surface, for instance, the fibrin clot formation occurred after 5 to 8 minutes. Plasma recalcification time on dextran sulfate-modified surfaces was also significantly lower than on unmodified chitosan. In the intrinsic coagulation pathway, factor XI or XII is autoactivated when in contact with negatively charged surfaces. Several studies have shown that factor XI or XII can be autoactivated by surface-bound heparin and dextran sulfate leading to fibrin clot formation.

Thus it can be seen that chitosan surfaces can be permanently modified in accordance with the invention to improve blood compatibility of chitosan. When in contact with blood, the modified surface resists plasma protein adsorption and cell adhesion.

TABLE 1

Swelling and thickness of chitosan membranes in acetic acid and phosphate-buffered saline[a].

| Swelling Medium | % Water Uptake | Thickness ($\mu$m) |
|---|---|---|
| Acetic Acid | 71.9 ± 4.87 | 62.3 ± 0.96 |
| Phosphate-Buffered Saline | 38.4 ± 1.29 | 47.0 ± 5.23 |

[a]Chitosan membranes were swollen in 10 mM acetic acid or phosphate-buffered saline (pH 7.4) for 10 minutes at room temperature.

TABLE 2

Permeability coefficients of different molecular weight analytes through control and surface-modified chitosan membranes.

| Membrane Type | Permeability Coefficient × $10^5$ ($cm^2$/min) | | | | |
|---|---|---|---|---|---|
| | Urea | Creatinine | Glucose | Vitamin B-2 | Vitamin B-12 |
| Cuprophan[a] | 5.435 ± 0.040 | 3.926 ± 0.060 | 2.480 ± 0.031 | 0.652 ± 0.007 | 0.484 ± 0.009 |
| Chitosan | 5.429 ± 0.023 | 4.045 ± 0.062 | 1.950 ± 0.027 | 0.618 ± 0.009 | 0.099 ± 0.002 |
| Chitosan-Heparin (2.5)[b] | 5.324 ± 0.012 | 4.032 ± 0.042 | 1.563 ± 0.019 | 0.410 ± 0.010 | 0.089 ± 0.001 |
| Chitosan-Heparin (10) | 5.330 ± 0.043 | 3.954 ± 0.051 | 1.545 ± 0.023 | 0.440 ± 0.012 | 0.085 ± 0.005 |
| Chitosan-DexSO$_4$ (2.5)[c] | 5.430 ± 0.036 | 4.067 ± 0.019 | 1.630 ± 0.017 | 0.494 ± 0.014 | 0.038 ± 0.002 |
| Chitosan-DexSO$_4$ (10) | 5.432 ± 0.026 | 3.468 ± 0.031 | 1.010 ± 0.015 | 0.264 ± 0.008 | 0.004 ± 0.000 |

[a]Commercially available cellulose hemodialysis membrane (Cuprophan ®) was used as a control.
[b]Chitosan membrane surface was modified with heparin (Ave. Mol. Wt. 15,000 daltons) at a bulk concentrations of 2.5 mg/ml and 10 mg/ml.
[c]Chitosan membrane surface was modified with dextran sulfate (Ave. Mol. Wt. 500,000 daltons) at a bulk concentrations of 2.5 mg/ml and 10 mg/ml.

TABLE 3

The concentration of serum complement component iC3b in contact with control and surface-modified chitosan membranes[a].

| Membrane Type | iC3b Concentration ($\mu$g/ml) |
|---|---|
| Cuprophan[b] | 101.5 ± 3.25 |
| Chitosan | 63.2 ± 4.23 |
| Chitosan-Heparin (2.5) | 59.6 ± 2.89 |
| Chitosan-Heparin (10) | 51.4 ± 5.43 |

TABLE 3-continued

The concentration of serum complement component iC3b in contact with control and surface-modified chitosan membranes[a].

| Membrane Type | iC3b Concentration ($\mu$g/ml) |
|---|---|
| Chitosan-DexSO$_4$ (2.5) | 61.9 ± 3.26 |
| Chitosan-DexSO$_4$ (10) | 57.5 ± 8.52 |

[a]The concentration of iC3b in serum was measured using a commercially available enzyme immunoassay. The average iC3b concentration of serum incubated for 1 h at 37° C. in the absence of membranes was 46.3 $\mu$g/ml.
[b]Cuprophan, chitosan, and surface-modified chitosan membranes were incubated with serum for 1 h at 37° C.

TABLE 4

Number of adherent platelets per 25,000 $\mu m^2$ on control and surface-modified chitosan membranes[a].

| Membrane Type | Number of Platelets/25,000 $\mu m^2$ |
|---|---|
| Cuprophan | 39.8 ± 9.24 |
| Chitosan | 57.2 ± 13.3 |
| Chitosan-Heparin (2.5) | 13.3 ± 5.03 |
| Chitosan-Heparin (10) | 10.9 ± 3.29 |
| Chitosan-DexSO$_4$ (2.5) | 8.4 ± 1.93 |
| Chitosan-DexSO$_4$ (10) | 8.6 ± 2.27 |

[a]Platelets in platelet-rich plasma were allowed to adhere and activate on Cuprophan, chitosan, and surface-modified chitosan membranes for 1 h at room temperature.

TABLE 5

Plasma recalcification time in contact with control and surface-modified chitosan membranes[a]

| Membrane Type | Plasma Recalcification Time (Minutes) |
|---|---|
| Cuprophan | 9.80 ± 0.44 |
| Chitosan | 9.34 ± 0.36 |
| Chitosan-Heparin (2.5) | 5.05 ± 0.55 |
| Chitosan-Heparin (10) | 7.90 ± 0.47 |

TABLE 5-continued

Plasma recalcification time in contact with control and surface-modified chitosan membranes[a]

| Membrane Type | Plasma Recalcification Time (Minutes) |
| --- | --- |
| Chitosan-DexSO$_4$ (2.5) | 5.22 ± 0.18 |
| Chitosan-DexSO$_4$ (10) | 4.70 ± 0.44 |

[a]Plasma recalcification time was measured with calcium chloride-containing citrated human plasma.

EXAMPLE 2

A. Materials

Chitosan with a degree of deacetylation of 87% and an average molecular weight of 750,000 daltons was obtained from Pronova Biopolymers (Raymond, Wash.). Methoxypoly(ethylene glycol) (MPEG) with an average molecular weight of 5,000 daltons was purchased from Fluka Chemika-Biochemika (Ronkonkoma, N.Y.). Chlorosulfonic acid was purchased from Aldrich Chemicals (Milwaukee, Wis.). Deionized distilled water (DDW, NANOpure II, Barnsted/Thermolyne, Dubuque, Iowa) was used exclusively to prepare all aqueous solutions. All other reagents and chemicals were of analytical grade or better.

B. Synthesis of Methoxypoly(Ethylene Glycol) Sulfonate

The terminal hydroxyl group of MPEG was reacted with chlorosulfonic acid to form MPEG sulfonate. Typically, 5.0 g (1.0 mmole) of MPEG was added to 100 ml of dry dimethylformamide containing 1.0% (w/v) triethanolamine. After complete dissolution, 0.58 g (5.0 mmoles) of chlorosulfonic acid was added dropwise to the MPEG solution. With continuous stirring, the reaction for conversion of the terminal hydroxyl group of MPEG into sulfonate proceeded for 10 hours under reflux conditions. MPEG sulfonate was precipitated in diethyl ether and washed extensively with diethyl ether. The polymer was dried in vacuum. The reaction yield was approximately 90%.

C. Chitosan Surface Modification

Glass microscope slides (25×75 mm) were washed with 2.0% (w/v) Isoclean® solution at 50° C. for 3 h. After rinsing with DDW, clean glass slides were dried at 60° C. Glass slides were coated with chitosan from a 1.0% (w/v) solution of the polymer in 0.1M acetic acid. Chitosan acetate film with DDW, the chitosan-coated slide was placed in 10 mM acetic acid solution for 10 minutes to induce ionization and swelling in the polymer film. MPEG sulfonate was dissolved in DDW to prepare a 10 mg/ml solution. The chitosan-coated slide was transferred into the MPEG sulfonate solution. Following a brief period (~30 seconds) of polyelectrolyte complexation and interpenetration of the MPEG sulfonate into the chitosan matrix, sodium hydroxide was added to collapse the chitosan film and permanently immobilize the anionic PEG derivative onto the chitosan surface. MPEG sulfonate-modified chitosan slide was washed with DDW and stored in phosphate-buffered saline (PBS, pH 7.4) containing 0.02% (w/v) sodium azide as a preservative at 4° C.

D. Characterization of MPEG Sulfonate-Modified Chitosan

Clean glass slides, chitosan-coated glass, and MPEG sulfonate-modified chitosan surfaces were analyzed by ESCA as in Example 1 to measure the surface elemental composition and the identity of the chemical functional groups. The identity of chemical functional groups was obtained by high resolution peak analysis of carbon-1s (C1s), oxygen-1s (O1s), nitrogen-1s (N1s) and sulfur-2p (S2p) envelopes.

E. Platelet Adhesion and Activation on MPEG Sulfonate-Modified Chitosan

An observation chamber for adherent platelets was assembled consisting of clean glass slide, chitosan-coated slide, or MPEG sulfonate-modified chitosan slide, two polyethylene spacers, and a glass coverslip. Human blood, obtained from healthy volunteers after informed consent, was collected in heparin-containing evacuated containers (Vacutainers®). Heparinized blood was centrifuged at 100 g for 10 minutes to obtain platelet-rich plasma (PRP). Two hundred $\mu$l of PRP was instilled into the platelet observation chamber. Platelets in PRP were allowed to adhere and activate on the control and surface-modified chitosan slides for 1 h at room temperature. Non-adherent platelets and plasma proteins were removed by washing the chamber with PBS. Adherent platelets were fixed, stained and observed as in Example 1.

F. Plasma Recalcification Time Measurements

Plasma recalcification time measurement, an indicator of the intrinsic coagulation reaction, is a useful marker of the interactions of blood on biomaterials surfaces. Plasma recalcification time measurements were carried out as in Example 1.

RESULTS

Platelet Adhesion and Activation

The extent of platelet adhesion and surface-induced activation is considered an early indicator of the thrombogenicity of blood-contacting biomaterials. The number of adherent platelets and the extent of platelet activation was significantly reduced on MPEG sulfonate-modified chitosan, as seen in Table 6. On the average, only 3.0 contact-adherent platelets per 25,000 $\mu m^2$ were found on the modified surface. Surface modification with MPEG sulfonate was very effective in preventing platelet adhesion and activation.

Plasma Recalcification Time

Plasma recalcification time, a measure of the intrinsic coagulation mechanism, indicates the time required for fibrin clot formation in calcium-containing citrated plasma. Since the time required for contact activation of plasma varies with the type of surface, the plasma recalcification time is also a useful indicator of blood-biomaterial interactions. Plasma recalcification time on glass surface, as shown in Table 7, was about 5.67 minutes. Glass, like other negatively-charged surfaces, is a potent activator of the intrinsic coagulation reaction. Chitosan-coated glass increased the plasma recalcification time to about 11.0 minutes. The significant increase in the time required for fibrin clot formation on chitosan suggest that this surface does not readily activate the intrinsic coagulation mechanism. Surface modification of chitosan with MPEG sulfonate also did not readily activate the intrinsic coagulation reaction. The plasma recalcification time on MPEG sulfonate-modified chitosan was 11.5 minutes. Prevention of the interactions between plasma proteins and the surface by the MPEG chains increases the time required for fibrin clot formation.

TABLE 6

Number of adherent platelets per 25,000 $\mu m^2$ on control and methoxypoly(ethylene glycol) sulfonate-modified chitosan surfaces[a].

| Surface Type | Number of Platelets/25,000 $\mu m^2$ |
|---|---|
| Clean Glass | 147.8 ± 35.2[b] |
| Chitosan-Coated Glass | 66.8 ± 12.1 |
| MPEG Sulfonate-Modified Chitosan | 3.00 ± 1.65 |

[a]Platelets in platelet-rich plasma (PRP) were allowed to adhere and activate on the control and methoxypoly(ethylene glycol) sulfonate (MPEG sulfonate)-modified chitosan surfaces for 1 h at room temperature.
[b]Mean ± S.D. (n = 12).

TABLE 7

Plasma recalcification time on control and methoxypoly(ethylene glycol) sulfonate-modified chitosan surfaces[a.]

| Surface Type | Time (Minutes) |
|---|---|
| Clean Glass | 5.67 ± 0.79[b] |
| Chitosan-Coated Glass | 11.0 ± 0.24 |
| MPEG Sulfonate-Modified Chitosan | 11.5 ± 0.32 |

[a]Glass test tube was coated with chitosan and modified with methoxypoly(ethylene glycol) sulfonate (MPEG sulfonate). Calcium-containing citrated human plasma was placed in the test tube and incubated at 37° C. The time, in minutes, required for fibrin clot formation was determined.
[b]Mean ± S.D. (n = 5)

What is claimed is:

1. An article of manufacture that is resistant to plasma protein adsorption, platelet adhesion, and thrombus formation, said article comprising a cationic polymer matrix which has been surface-modified by a method comprising, in the order given, the steps of:
   a. swelling a cationic polymer matrix in a medium having a pH value <7;
   b. removing the swelled cationic polymer matrix from said medium;
   c. applying a surface-modifying agent to an entire surface of said cationic polymer matrix to form a mixture; and
   d. adjusting the pH of said mixture to a value ≧7.

2. The article of manufacture of claim 1 wherein said surface-modifying agent is selected from the group consisting of anionic polysaccharides; anionic polyalkylene oxide derivatives; anionic polyalkylene glycol derivatives; polycarboxylic acids; anionic surfactants; anionic phospholipids; carboxyalkylcelluloses; and mixtures thereof.

3. The article of manufacture of claim 1 wherein said article is a planar or hollow fiber membrane.

4. The article of manufacture of claim 1 wherein said article is a surgical article selected from the group consisting of films, sponges, and sutures.

5. The article of manufacture of claim 1 wherein said article is in the form of microcapsules for in vivo cell therapy.

6. The article of manufacture of claim 1 wherein said article is in the form of microspheres or nanospheres for immunoadsorption and drug delivery.

7. The article of manufacture of claim 1 wherein said article is a bone paste.

8. The article of manufacture of claim 1 wherein said article is a stent.

9. The article of manufacture of claim 1 wherein said surface-modifying agent is selected from the group consisting of heparin, dextran sulfate, alginic acid, hyaluronic acid, MPEG sulfonate, carboxymethylcellulose, and acid-modified polyethylene oxide.

10. A method of preparing a biocompatible cationic polymer-containing article that is resistant to plasma protein adsorption, platelet adhesion, or thrombus formation, comprising, in the order given, the steps of:
    a. placing a cationic polymer matrix-containing article in a medium having a pH value <7 and swelling said polymer matrix;
    b. removing the swelled cationic polymer matrix-containing article from said medium;
    c. applying a surface-modifying agent to an entire surface of said cationic polymer matrix-containing article to form a mixture; and
    d. adjusting the pH of said mixture to a value ≧7.

11. The article of manufacture of claim 1 wherein said cationic polymer is selected from the group consisting of chitosan, cationic cellulosic derivatives, and cationic polyacrylates.

12. The article of manufacture of claim 1 wherein said cationic polymer is selected from the group consisting of chitosan, cationic cellulosic derivatives, and cationic polyacrylates, and said surface-modifying agent is selected from the group consisting of anionic polysaccharides; anionic polyalkylene oxide derivatives; anionic polyalkylene glycol derivatives; polycarboxylic acids; anionic surfactants; anionic phospholipids; carboxyalkylcelluloses; and mixtures thereof.

13. The article of manufacture of claim 1 wherein said cationic polymer is chitosan and said surface-modifying agent is selected from the group consisting of heparin, dextran sulfate, and MPEG sulfonate.

14. The article of manufacture of claim 13 wherein said surface-modifying agent has been applied at a concentration of about 2.5–10 mg/ml.

15. The article of manufacture of claim 1 wherein said surface-modifying agent has been applied for a brief period of about 20–30 seconds.

16. The method of claim 10 wherein said cationic polymer is chitosan, and said surface-modifying agent is selected from the group consisting of heparin, dextran sulfate, and MPEG sulfonate.

17. The method of claim 16 wherein said surface-modifying agent is applied at a concentration of about 2.5–10 mg/ml.

18. The method of claim 10 wherein said surface-modifying agent is applied for a brief period of about 20–30 seconds.

* * * * *